(12) United States Patent
Fischer et al.

(10) Patent No.: US 7,217,847 B2
(45) Date of Patent: May 15, 2007

(54) METHOD FOR THE PRODUCTION OF OPTICALLY ACTIVE 2-AMINO 2-CHLORO, 2 HYDROXY OR 2-ALKOXY-1-ALCOHOLS

(75) Inventors: Rolf-Hartmuth Fischer, Heidelberg (DE); Nils Bottke, Mannheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 170 days.

(21) Appl. No.: 10/524,850

(22) PCT Filed: Aug. 28, 2003

(86) PCT No.: PCT/EP03/09513

§ 371 (c)(1),
(2), (4) Date: Feb. 18, 2005

(87) PCT Pub. No.: WO2004/022522

PCT Pub. Date: Mar. 18, 2004

(65) Prior Publication Data

US 2006/0116521 A1 Jun. 1, 2006

(30) Foreign Application Priority Data

Sep. 4, 2002 (DE) ................. 102 41 292

(51) Int. Cl.
*C07C 29/156* (2006.01)
*C07C 27/04* (2006.01)
*C07C 213/00* (2006.01)
*C07C 209/78* (2006.01)

(52) U.S. Cl. ............. 568/814; 568/885; 564/358; 564/503

(58) Field of Classification Search ............. None
See application file for complete search history.

(56) References Cited

U.S. PATENT DOCUMENTS

| 4,214,106 A | 7/1980 | Freudenberger et al. |
| 5,536,879 A | 7/1996 | Antons et al. |
| 5,698,749 A | 12/1997 | Perdersen et al. |
| 5,731,479 A | 3/1998 | Antons |
| 5,969,164 A | 10/1999 | Budge et al. |
| 6,204,417 B1 | 3/2001 | Fischer et al. |
| 6,310,254 B1 | 10/2001 | Antons et al. |
| 6,355,848 B1 | 3/2002 | Antons et al. |
| 6,376,414 B1 | 4/2002 | Antons et al. |
| 2001/0021781 A1 | 9/2001 | Hamashima et al. |

FOREIGN PATENT DOCUMENTS

| DE | 27 15 666 | 10/1978 |
| EP | 0 589 168 A2 | 3/1994 |
| EP | 0 696 575 B1 | 2/1996 |
| EP | 0 717 023 B1 | 6/1996 |
| EP | 0 848 991 B1 | 6/1998 |
| EP | 1 112 776 A1 | 7/2001 |
| WO | WO-98/52891 | 11/1998 |
| WO | WO-99/38613 | 8/1999 |
| WO | WO-99/38824 | 8/1999 |
| WO | WO-99/38838 | 8/1999 |

OTHER PUBLICATIONS

M. Studer et al., Adv. Synth. Catal. 2001, 343, pp. 802-808.
International Search Reported dated Feb. 2, 2004.

*Primary Examiner*—Brian Davis
(74) *Attorney, Agent, or Firm*—Connolly Bove Lodge & Hutz LLP

(57) ABSTRACT

The invention relates to a process for preparing optically active 2-amino-, 2-chloro-, 2-hydroxy- or 2-alkoxy-1-alcohols by catalytically hydrogenating appropriate optically active 2-amino-, 2-chloro-, 2-hydroxy- and 2-alkoxycarboxylic acids or their acid derivatives in the presence of catalysts comprising palladium and rhenium or platinum and rhenium.

18 Claims, No Drawings

METHOD FOR THE PRODUCTION OF OPTICALLY ACTIVE 2-AMINO 2-CHLORO, 2 HYDROXY OR 2-ALKOXY-1-ALCOHOLS

CROSS REFERENCE TO RELATED APPLICATION

The present application is a National Stage application of PCT/EP2003/009513, filed Aug. 28, 2003, which claims priority from German Patent Application No. DE 102 41 292.8, filed Sep. 4, 2002.

The present invention relates to an improved process for preparing optically active 2-amino-, 2-chloro-, 2-hydroxy- or 2-alkoxy-1-alcohols by catalytically hydrogenating optically active 2-amino-, 2-chloro-, 2-hydroxy- or 2-alkoxy-carboxylic acids or their acid derivatives.

As disclosed by EP-A-696 575 and EP-A-717 023, optically active 2-aminocarboxylic acids and 2-hydroxycarboxylic acids can be hydrogenated to optically active 2-amino-1-alkanols and 1,2-alkanediols in the presence of ruthenium catalysts such as elemental ruthenium, ruthenium oxides and hydroxides or ruthenium on supports. In a reaction between 80 and 100° C., an enantiomeric excess of up to 98.5% e.e. is maintained.

According to WO 99/38838, the yields and enantiomeric excesses of 2-amino-1-alkanols can also be increased by hydrogenating the corresponding 2-aminocarboxylic acids in the presence of mineral acids and ruthenium catalysts which comprise from one to two further elements of atomic number from 23 to 82. Particular preference is given to ruthenium/rhenium catalysts whose use leads to the retention of enantiomeric excesses of up to 99.9% e.e.

According to WO 99/38824, it is also possible to increase the yields and enantiomeric excesses of 1,2-alkanediols by using ruthenium catalysts which comprise one or two further elements of atomic numbers from 23 to 82. Particular preference is given to the addition of rhenium.

WO 99/38613 describes a process for preparing particularly advantageous catalysts which comprise ruthenium and at least one other element of atomic number from 23 to 82 and their use for hydrogenations. The process comprises combining a slurry of a ruthenium compound which has a specific surface area of from 50 to 300 m²/g with a solution of at least one metal compound. Particular preference is given to unsupported ruthenium/rhenium catalysts which are used for the preparation of optically active 2-aminoalcohols or 1,2-diols.

It is also known that optically active 2-amino- and 2-hydroxycarboxylic esters can be hydrogenated at 25° C. and 100 bar of hydrogen pressure in the presence of catalysts consisting of rhodium and platinum and a solvent to corresponding optically active 2-aminoalcohols or 1,2-diols with enantiomeric excesses of over 99.9% e.e. (M. Studer et al., Adv. Synth. Catal. 2001, 343, pages 802–808).

WO 98/52891 discloses the hydrogenation of aliphatic carboxylic acids, anhydrides, esters or lactones in the presence of platinum/rhenium catalysts which comprise a further element such as molybdenum, silver or palladium to the corresponding alcohols. This allows corrosion problems to be avoided.

It is an object of the present invention to provide an improved process for hydrogenating optically active 2-amino-, 2-chloro-, 2-hydroxy- and 2-alkoxycarboxylic acids and their acid derivatives to the corresponding optically active alcohols. The catalysts to be used for the hydrogenation should be easy to prepare, have a high activity and lead to high yields of productive value and enantiomeric excesses.

We have found that this object is achieved by a process for preparing optically active 2-amino-, 2-chloro-, 2-hydroxy- or 2-alkoxy-1-alkanols by catalytically hydrogenating appropriate optically active 2-amino-, 2-chloro-, 2-hydroxy- and 2-alkoxycarboxylic acids or their acid derivatives, which comprises carrying out the hydrogenation in the presence of catalysts comprising palladium and rhenium or platinum and rhenium.

In the process according to the invention, it is possible to use, for example, optically active carboxylic acids or their derivatives of the formula I

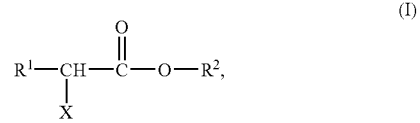

where the radicals are defined as follows:

$R^1$: straight-chain or branched $C_1$–$C_{12}$-alkyl, $C_7$–$C_{12}$-aralkyl or $C_6$–$C_{10}$-aryl, each of which may be substituted by $NR^3R^4$, OH, COOH and/or further groups stable under the reaction conditions, $R^2$: hydrogen, straight-chain or branched $C_1$–$C_{12}$-alkyl or $C_3$–$C_8$-cycloalkyl, X: chlorine, $NR^5R^6$ or $OR^7$, $R^3$, $R^4$, $R^5$ and $R^6$:
each independently hydrogen, straight-chain or branched $C_1$–$C_{12}$-alkyl, $C_7$–$C_{12}$-aralkyl, $C_6$–$C_{10}$-aryl, $C_3$–$C_8$-cycloalkyl or $C_3$–$C_8$-cycloalkyl in which one $CH_2$ group is replaced by O or $NR^8$, $R^3$ and $R^4$ and also $R^5$ and $R^6$:
also each independently together —$(CH_2)_m$—, where m is an integer from 4 to 7, $R^1$ and $R^5$:
also together —$(CH_2)_n$— where n is an integer from 2 to 6, $R^7$: hydrogen, straight-chain or branched $C_1$–$C_{12}$-alkyl or $C_3$–$C_8$-cycloalkyl, $R^1$ and $R^7$:
also together —$(CH_2)_n$—, where n is an integer from 2 to 6 and $R^8$: hydrogen, straight-chain or branched $C_1$–$C_{12}$-alkyl, $C_7$–$C_{12}$-aralkyl or $C_6$–$C_{10}$-aryl, or their acid anhydrides and hydrogenate them to the corresponding optically active alcohols.

The $R^1$ radicals may be widely varied and also bear, for example, from 1 to 3 substituents stable under the reaction conditions, such as $NR^3R^4$, OH and/or COOH.

Examples of $R^1$ radicals include:

$C_1$–$C_6$-alkyls such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, $C_1$–$C_{12}$-alkyl such as $C_1$–$C_6$-alkyl (mentioned above) or unbranched or branched heptyl, octyl, nonyl, decyl, undecyl or dodecyl, $C_7$–$C_{12}$-aralkyls such as phenylmethyl, 1-phenylethyl 2-phenylethyl, 1-phenylpropyl, 2-phenylpropyl or 3-phenylpropyl, $C_6$–$C_{10}$-aryls such as phenyl, naphthyl or anthracenyl, each of which may bear a substituent such as $NR^9R^{10}$, OH and/or COOH.

Examples of definitions of $R^2$ include the following:

hydrogen, straight-chain or branched $C_1$–$C_{12}$-alkyl (as specified above) or $C_3$–$C_8$-cycloalkyl, e.g. cyclopropyl, cyclobutyl, cyclopentyl, cyclohexyl, cycloheptyl and cyclooctyl.

Instead of the carboxylic ester, it is also possible to use acid anhydrides as carboxylic acid derivatives.

The X radical is chlorine, $NR^5R^6$ or $OR^7$ where $R^5$ and $R^6$, exactly like $R^3$ and $R^4$, or $R^9$ and $R^{10}$, are each independently hydrogen, straight-chain or branched $C_1$–$C_{12}$-alkyl, especially $C_1$–$C_6$-alkyl, $C_7$–$C_{12}$-aralkyl or $C_6$–$C_{10}$-aryl, especially phenyl, or $C_3$–$C_8$-cycloalkyl (each as specified above for the $R^1$ and $R^2$ radicals).

The $R^3$ and $R^4$, $R^5$ and $R^6$, and also $R^9$ and $R^{10}$ pairs may each be independently combined to form —$(CH_2)_m$— where m is an integer from 4 to 7, in particular 4 or 5. A $CH_2$ group may be replaced by O or $NR^8$.

The $R^1$ and $R^5$ radicals may also together be —$(CH_2)_n$— where n is an integer from 2 to 6.

The $R^7$ radical is preferably hydrogen or straight-chain or branched $C_1$–$C_{12}$-alkyl or $C_3$–$C_8$-cycloalkyl, more preferably methyl, ethyl, 1-methylethyl, 1,1-dimethylethyl, hexyl, cyclohexyl or dodecyl. It may also be —$(CH_2)_n$— together with $R^1$ where n is an integer from 2 to 6.

The hydrogenation according to the invention provides the corresponding optically active alcohols of the formula II

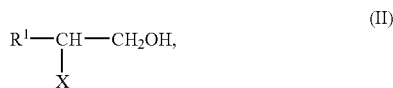

$$R^1\text{—CH—CH}_2\text{OH,} \quad \text{(II)}$$
$$|$$
$$X$$

where $R^1$ and X are each as defined above.

Examples of useful starting materials include 2-amino-, 2-chloro-, 2-hydroxy- or 2-alkoxycarboxylic acids and their derivatives where the $R^1$ radical, as long as it is inert under the reaction conditions, may be widely varied as described above.

Owing to the easy accessibility, preference is given to using 2-amino acids of the formula I such as phenylalanine, threonine, glutamic acid, proline, aspartic acid, alanine, ornithine, valine, leucine and isoleucine and their derivatives, and also 2-hydroxy- and 2-chlorocarboxylic acids such as tartaric acid, lactic acid, 2-chloropropionic acid and malic acid and derivatives thereof.

The catalysts used for the process according to the invention comprise palladium and rhenium or platinum and rhenium. They may be used for the hydrogenation according to the invention with or without catalyst support. They may additionally comprise at least one further element having an atomic number of from 23 to 82.

Further elements for this purpose include titanium, vanadium, chromium, manganese, iron, cobalt, nickel, copper, zinc, zirconium, molybdenum, silver, tin, tungsten, lead, lanthanum and cerium, preferably silver, tungsten, molybdenum and tin, more preferably silver and tin.

The weight ratio of platinum or palladium to rhenium is preferably from 100:1 to 0.01:1, more preferably from 50:1 to 0.05:1, in particular from 10:1 to 0.1:1. The weight ratio of platinum or palladium to the at least one further element is preferably from 100:1 to 10:1, more preferably from 50:1 to 20:1.

The catalysts used according to the invention may comprise palladium, platinum, rhenium and any additional elements in different forms, for example in elemental form, in the form of compounds of palladium, platinum, rhenium and the additional elements or in the form of an intermetallic compound of palladium, platinum, rhenium and the additional elements.

The catalyst may be used as an unsupported or supported catalyst. When it is used as a supported catalyst, the support material may be any suitable material, for example carbons, carbon blacks, graphites, silicon carbides, silicon dioxides, silicates, zeolites, titanium dioxide, zirconium dioxide and aluminas. These supported catalysts may comprise, for example, from 1 to 50% by weight of metal in elemental form or in the form of compounds. A particularly preferred support material is activated carbon pretreated oxidatively or with mineral acid. The preparation of such catalysts is described, for example, in EP-A-848 991 and U.S. Pat. No. 5,698,749.

If not applied to a support material, the catalysts may be used, for example, in colloidal form or as a finely divided solid in the manner according to the invention. Examples of catalysts include finely divided palladium/rhenium, platinum/rhenium, palladium/rhenium/silver, platinum/rhenium/silver, palladium/rhenium/molybdenum, platinum/rhenium/tungsten, platinum/rhenium/tin particles, for example in metallic form or in the form of their oxides, hydroxides, halides, nitrates, carboxylates, acetylacetonates or as amine complexes.

Particular preference is given to unsupported bimetallic palladium/rhenium or platinum/rhenium catalysts. These may also additionally comprise at least one further element of atomic number from 23 to 82. They may be prepared, for example, by reduction of mixtures of platinum oxide or palladium oxide and rhenium oxide with a reducing agent, for example hydrogen. A third metal may be deposited in the preparation of the catalyst or in situ, during the hydrogenation reaction. The preparation of such catalysts is described, for example, in WO 98/52891.

In a preferred embodiment of the process according to the invention, the above-described optically active starting materials are hydrogenated in the presence of an organic or inorganic acid. In general, the addition of acid is from 0.5 to 1.5 equivalents, more preferably from 1 to 1.3 equivalents, based on 1 equivalent of any basic group present in the starting materials. Examples of useful organic acids include acetic acid, propionic acid and adipic acid. Preference is given to adding inorganic acids, especially sulfuric acid, hydrochloric acid and phosphoric acid. The acids may be used, for example, as such, in the form of aqueous solutions or in the form of their separately prepared salts with the starting materials to be hydrogenated, for example as sulfates, hydrogensulfates, hydrochlorides, phosphates, mono- or dihydrogenphosphates.

Based on 1 mol of optically active starting compound used, it is possible to use, for example, from 0.1 to 10 g of the catalysts used according to the invention comprising platinum or palladium, rhenium and optionally additional metals or from 1 to 50 g of the supported catalysts.

In general, the process according to the invention is carried out in the presence of a solvent for the optically active starting materials of the formula I. Examples of useful solvents include water, water-miscible organic solvents and mixtures of both. Useful water-miscible solvents include lower alcohols having from 1 to 4 carbon atoms and water-miscible ethers, e.g. tetrahydrofuran or dioxane. Preferred solvents are water and mixtures which comprise water and lower alcohols and/or tetrahydrofuran.

The process according to the invention may be carried out, for example, at temperatures in the range from 30 to 140° C. and pressures in the range from 5 to 300 bar. Preference is given to temperatures from 50 to 130° C. and pressures from 10 to 280 bar. Particular preference is given to temperatures from 60 to 120° C. and pressures from 50 to 250 bar.

The reaction is over when no more hydrogen is taken up. Typically, the hydrogenation time is from 0.5 to 8 hours.

To work up the reaction mixture, it may, for example, be initially cooled, the catalyst may be removed, for example by filtration, and the volatile constituents present such as solvent and water of reaction may be partly or fully removed by distillation, optionally under reduced pressure. In the case of 2-aminocarboxylic acids as starting compounds, it is possible to release the aminoalcohol from its salt from the residue with base, e.g. aqueous alkali metal hydroxide solution or alcoholic alkoxide solution, remove the precipitated salt and fractionate the filtrate under reduced pressure. Like the solvent, the catalyst removed can be reused.

The process according to the invention may be carried out continuously, semicontinuously or batchwise.

EXAMPLES

General Hydrogenation Procedure

In a metal autoclave, 0.1 g of $PtO_2$ and 0.2 g of $Re_2O_7$, suspended in 9 g of water, are initially charged and compressed with 60 bar of hydrogen. The suspension is stirred at 270° C. for 1 hour and decompressed after cooling, and 1 g of the compound to be hydrogenated is added. Hydrogenation is then effected under the conditions specified below.

Inventive Examples 1 to 3

Preparation of (S)-leucinol

In accordance with the procedure given, 1 g of enantiomerically pure (L)-leucine (99.9% e.e.) was hydrogenated together with 0.5 g of concentrated sulfuric acid. The reaction conditions are summarized in Table 1:

TABLE 1

| Inv. example | Pressure [bar] | Temperature [° C.] | Reaction time [h] |
|---|---|---|---|
| 1 | 100 | 60 | 5 |
| 2 | 100 | 80 | 5 |
| 3 | 100 | 100 | 5 |

To determine the enantiomeric excesses, samples of the reaction effluents were neutralized with sodium hydrogencarbonate, trifluoroacetylated and subsequently analyzed by means of gas chromatography using a chiral Cyclodex GTA column. The enantiomeric excesses in all three examples were determined to be greater than 99% e.e.

Inventive Example 4

Preparation of (S)-1,2-propanediol

In accordance with the procedure given above, 1 g of enantiomerically pure (L)-lactic acid (99.9% e.e.) was hydrogenated at a temperature of 80° C. and 200 bar of hydrogen pressure for 5 hours.

The enantiomeric excess of the reaction effluent was determined by means of gas chromatography using a Chirasil-Dex capillary to be greater than 99% e.e.

Inventive Example 5

Preparation of S-1,2,4-butanetriol

A metal autoclave was initially charged with a suspension of 1.6 g of $PtO_2$ and 4 g of $Re_2O_7$ in 50 g of water which was pressurized with 60 bar of hydrogen and stirred at 270° C. and 124 bar for 1 hour. After cooling, the mixture was decompressed, 24 g of L(−)-malic acid in 100 ml of water were added and hydrogenation was subsequently effected at 100° C. and a pressure of 250 bar for 12 hours. S-1,2,4-butanetriol was obtained in a yield of 40.8% and with an enantiomeric excess of 97.2% e.e.

Inventive Example 6

Preparation of S-alaninol

A metal autoclave was initially charged with a suspension of 0.4 g of $PtO_2$ and 1 g of $Re_2O_7$ in 50 g of water which was pressurized with 60 bar of hydrogen and stirred at 270° C. and 125 bar for 1 hour. After cooling, the mixture was decompressed, 24 g of L-alanine and 13.8 g of concentrated sulfuric acid in 100 ml of water were added and hydrogenation was subsequently effected at 60° C. and a pressure of 200 bar for 12 hours. At a conversion of 14%, alaninol was obtained with an enantiomeric excess of 99.4% e.e.

Comparative Example 1

Hydrogenation of Enantiomerically Pure (L)-lactic Acid Without $Re_2O_7$

Inventive example 4 was carried out under the given reaction conditions but with the omission of 0.2 g of $Re_2O_7$. The gas chromatography analysis showed that only about 1% of the (L)-lactic acid had been converted to 1,2-propanediol.

We claim:

1. A process for preparing optically active 2-amino-, 2-chloro-, 2-hydroxy- or 2-alkoxy-1-alkanols by catalytically hydrogenating optically active 2-amino-, 2-chloro-, 2-hydroxy- and 2-alkoxycarboxylic acids or their acid derivatives, which comprises carrying out the hydrogenation in the presence of catalysts comprising palladium and rhenium or platinum and rhenium.

2. The process according to claim 1, wherein optically active 2-amino-, 2-chloro-, 2-hydroxy- or 2-alkoxycarboxylic acids or their esters of the formula I

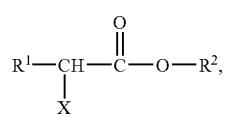

(I)

where the radicals are defined as follows:

R$^1$: straight-chain or branched C$_1$–C$_{12}$-alkyl, C$_7$–C$_{12}$-aralkyl or C$_6$–C$_{10}$-aryl, each of which may be substituted by NR$^3$R$^4$, OH, and/or COOH, R$^2$: hydrogen, straight-chain or branched C$_1$–C$_{12}$-alkyl or C$_3$–C$_8$-cycloalkyl, X: chlorine, NR$^5$R$^6$ or OR$^7$, R$^3$, R$^4$, R$^5$ and R$^6$: each independently hydrogen, straight-chain or branched C$_1$–C$_{12}$-alkyl, C$_{12}$–C$_{12}$-aralkyl, C$_6$–C$_{10}$-aryl, C$_3$–C$_8$-cycloalkyl or C$_3$–C$_8$-cycloalkyl in which one CH$_2$ group is replaced by O or NR$^8$, R$^3$ and R$^4$ and also R$^5$ and R$^6$: also each independently together —(CH$_2$)$_m$—, where in is an integer from 4 to 7, R$^1$ and R$^5$: also together —(CH$_2$)$_n$— where n is an integer from 2 to 6, R$^7$: hydrogen, straight-chain or branched C$_1$–C$^{12}$-alkyl or C$_3$–C$_8$-cycloalkyl, R$^1$ and R$^7$: also together —(CH$_2$)$_n$—, where n is an integer from 2 to 6 and R$^8$: hydrogen, straight-chain or branched C$_1$–C$_{12}$-alkyl, C$_7$–C$_{12}$-aralkyl or C$_6$–C$_{10}$-aryl, or their acid anhydrides are used and hydrogenated to the corresponding optically active alcohols of formula II

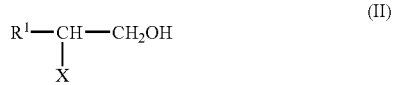

(II)

in which R$^1$ and X are each as defined above.

3. The process according to claim 1, wherein the palladium/rhenium or platinum/rhenium catalysts comprise at least one element from the group of the elements titanium, vanadium, chromium, manganese, iron, cobalt, nickel, copper, zinc, zirconium, molybdenum, silver, tin, tungsten, lead, lanthanum and cerium.

4. The process according to claim 1, wherein the palladium/rhenium or platinum/rhenium catalysts comprise at least one element from the group of the elements silver, molybdenum, tungsten and tin.

5. The process according to claim 1, wherein the palladium/rhenium or platinum/rhenium catalysts are used unsupported or applied to a support.

6. The process according to claim 1, wherein the weight ratio of the palladium or platinum to rhenium is from 100:1 to 0.01:1.

7. The process according to claim 1, wherein the weight ratio of the palladium or platinum to rhenium is from 50:1 to 0.05:1.

8. The process according to claim 3, wherein the weight ratio of the palladium or platinum to the at least one element from the group of elements is from 100:1 to 10:1.

9. The process according to claim 1, wherein the hydrogenation is carried out in the presence of an acid.

10. The process according to claim 1, wherein the hydrogenation is carried out at a temperature of from 30° to 140° C.

11. The process according to claim 2, wherein the compound of formula I is selected from the group consisting of phenylalanine, threonine, glutamic acid, praline, aspartic acid, alanine, ornithine, valine, leucine, isoleucine, taz-taric acid, lactic acid, 2-chloropropionic acid, malic acid and the acid derivatives of each thereof.

12. The process according to claim 4, wherein the weight ratio of the palladium or platinum to the at least one element from the group of elements is from 100:1 to 10:1.

13. The process according to claim 4, wherein the hydrogenation is carried out in the presence of an acid and at a temperature of from 30° to 140° C.

14. The process according to claim 1, wherein the 2-aminocarboxylic acids are selected from the group consisting of phenylalanine, threonine, glutamic acid, proline, aspartic acid, alanine, ornithine, valine, leucine, isoleucine, the 2-hydroxycarboxylic acids are selected from tartaric acid, lactic acid or malic acid, and the 2-chlorocarboxylic acid is 2-chloropropionic acid.

15. The process according to claim 1, wherein the weight ratio of the palladium or platinum to rhenium is from 10:1 to 0.1:1.

16. The process according to claim 4, wherein the weight ratio of the palladium or platinum to rhenium is from 10:1 to 0.1:1.

17. A process for preparing optically active 2-amino-, 2-chloro-, 2-hydroxy- or 2-alkoxy-1-alkanols by catalytically hydrogenating optically active, 2-substituted-carboxylic acids selected from the group consisting of 2-amino-, 2-chloro-, 2-hydroxy- and 2-alkoxycarboxylic acids or the acid derivatives of each thereof, which comprises carrying out the hydrogenation in the presence of an unsupported bimetallic catalyst comprising palladium and rhenium or platinum and rhenium, wherein the catalysts are prepared from the mixtures of platinum oxide or palladium oxide, and rhenium oxide in the presence of a reducing agent.

18. The process according to claim 17, wherein the 2-aminocarboxylic acids are selected from the group consisting of phenylalanine, threonine, glutaric acid, proline, aspartic acid, alanine, ornithine, vaunt, leucine, isoleucine, the 2-hydroxycarboxylic acids are selected from tartaric acid, lactic acid or malic acid, and the 2-chlorocarboxylic acid is 2-chloropropionic acid.

* * * * *